United States Patent [19]
Levin

[11] Patent Number: 5,260,487
[45] Date of Patent: Nov. 9, 1993

[54] PROCESS FOR THE PREPARATION OF 2-HYDROXYARYLALDEHYDES

[75] Inventor: Daniel Levin, Worsley, England

[73] Assignee: Imperial Chemical Industries PLC, London, England

[21] Appl. No.: 932,296

[22] Filed: Aug. 19, 1992

[30] Foreign Application Priority Data

Aug. 23, 1991 [GB] United Kingdom ............... 9118198
Aug. 23, 1991 [GB] United Kingdom ............... 9118222
Jun. 5, 1992 [GB] United Kingdom ............... 9211907

[51] Int. Cl.$^5$ ............................................ C07C 45/00
[52] U.S. Cl. .................................. 568/433; 568/425; 568/426; 568/435
[58] Field of Search ............... 568/485, 420, 433, 458, 568/426, 435, 425

[56] References Cited

U.S. PATENT DOCUMENTS 4,231,967 11/1980 Matsuda et al. ................... 568/433
4,638,096 1/1987 Virnig .............................. 568/433

FOREIGN PATENT DOCUMENTS 2104516 3/1983 European Pat. Off. .
0077279 4/1983 European Pat. Off. ............ 568/433
0106653 4/1984 European Pat. Off. ............ 568/433
2163157 2/1986 United Kingdom ............... 568/433

OTHER PUBLICATIONS

G. Casiraghi et al., "Selective Reactions Using Metal Phenoxides. Part I, Reactions with Formaldehyde" Journal of the Chemical Society, Perkin Transactions 1 1978, Letchworth GB, pp. 318–321.

Primary Examiner—Werren B. Lone
Attorney, Agent, or Firm—Cushman, Darby & Cushman

[57] ABSTRACT

A method for the preparation of a 2-hydroxyarylaldehyde which comprises reacting a magnesium bis-hydrocarbyloxide derived at least in part from a hydroxyaromatic compound having at least one free position ortho to the hydroxyl group with formaldehyde or formaldehyde-liberating compound under substantially anhydrous conditions.

22 Claims, No Drawings

PROCESS FOR THE PREPARATION OF 2-HYDROXYARYLALDEHYDES

This invention relates to a chemical process and more particularly to a method for the preparation of 2-hydroxyarylaldehydes.

A number of 2-hydroxyarylaldehydes are known as useful products in the perfume and agricultural chemical industries and especially as intermediates for the corresponding oximes which are used as metal extractants.

Methods that have been described for the production of 2-hydroxyarylaldehydes have included, in particular, the ortho-formulation of a phenol having a free ortho position using formaldehyde or a formaldehyde-liberating compound in the presence of a suitable ortho-selective catalyst, the reaction generally being performed at an elevated temperature in an anhydrous organic solvent. Catalysts proposed for this reaction include tin, chromium, iron, titanium, zirconium and aluminium compounds, often with the additional use of a nitrogen base as catalyst promoter. In this connection, reference can be made to GB-A-2163157, U.S. Pat. No. 4,231,967, EP-A-0077279 and EP-A-0106653. Whilst these processes can give good yields of hydroxy-aldehyde, many of the catalysts and/or promoters used are costly and/or toxic materials requiring special handling on an industrial scale. Additionally, some of the processes require the use of pressure.

In J. C. S. Perkin I, 1978, 318, Casiraghi et al describe the reaction of formaldehyde with aryloxymagnesium bromides to give 2,2'-dihydroxydiphenylmethanes and with aryloxymagnesium bromidehexamethylphosphoramide 1:1 complexes to give 2-hydroxybenzaldehydes, the reactions being performed in refluxing benzene.

Whilst the process described by Casiraghi et al gives 2-hydroxybenzaldehydes in high yield and selectivity, its suitability for industrial exploitation is limited because of its use of a costly Grignard reagent in conjunction with the highly toxic hexamethylphosphoramide and benzene. These limitations have been acknowledged by Casiraghi et al in J. C. S. Perkin I, 1980, 1862.

It has now be en found that 2-hydroxyarylaldehydes can be prepared in high yield if the aryloxymagnesium bromide is replaced by a less expensive magnesium bis-hydrocarbyloxide as hereinafter defined and that the use of hexamethylphosphoramide and benzene can be avoided. Furthermore, if a bis-aryloxide is used instead of said Grignard reagent, the usage of magnesium relative to the other reactants can be halved.

Accordingly, the invention provides a method for the preparation of a 2-hydroxyarylaldehyde which comprises reacting a magnesium bis-hydrocarbyloxide derived at least in part from a hydroxyaromatic compound having at least one free position ortho to the hydroxyl group with formaldehyde or a formaldehyde-liberating compound under substantially anhydrous conditions.

The reaction on which the method of the invention is based is suitably performed at temperatures within the range from about 60° to about 130° C., for example 80°–1200° C. Somewhat lower reaction temperatures can also be used but will generally result in longer reaction times whilst higher reaction temperatures may lead to increased side reactions and, therefore, to a less pure product. The reaction is preferably carried out at atmospheric pressure but higher pressures may be employed if desired. By-products of the reaction, for example methanol, methyl formate and methylal, may be removed from the reaction mixture as they are formed, using conventional procedures.

The substantially anhydrous conditions required by the reaction may be conveniently provided by the use of substantially anhydrous reactants together with a substantially anhydrous solvent system. Suitable solvent systems typically comprise an inert non-polar or low polarity organic solvent, preferably used in conjunction with a co-solvent.

Suitable inert solvents include aromatic hydrocarbons, for example xylene, mesitylene, cumene, cymene, tetralin and, especially, toluene and chlorinated aromatic hydrocarbons, for example chlorobenzene and o-dichlorobenzene. Mixtures of inert solvents may be used.

Suitable co-solvents include compounds capable of acting as ligands with respect to magnesium atoms. Such compounds include polar solvents, and/or proton acceptors. As examples of suitable co-solvents, there may be mentioned polar aprotic solvents such as dimethylsulphoxide, sulpholane, dimethylacetamide, N-formylpiperidine, N-methylpyrrolidinone, tetramethylurea and, especially, dimethylformamide, tertiary bases such as triethylamine, tri-octylamine, tetramethylethylenediamine and pyridine, ethers such as diethyl ether, diphenyl ether, tetrahydrofuran, glyme, diglyme, triglyme, tris[2-(2-methoxyethoxy)ethyl]amine and crown ethers and other polar solvents such as "Polymeg" 1000 and "Cellosolve" and the like. Particularly useful co-solvents include lower alkanols such as ethanol and, especially, methanol. Mixtures of co-solvents may be used. The co-solvent may be incorporated into the reaction mixture as such or in the form of a ligand already complexed with the magnesium atoms of the bis-aryloxide.

Some solvent materials may have the ability to function as both "solvent" and "co-solvent" in the method of the invention. Thus, for example, a low polarity material such as tetrahydrofuran may be used as a solvent in conjunction with a higher polarity co-solvent or as a co-solvent in conjunction with a lower polarity solvent or it may be used as the sole solvent/co-solvent.

Magnesium bis-hydrocarbyloxides which may be used in the method of the invention are compounds containing two hydrocarbyloxy residues per magnesium atom, at least one of said hydrocarbyloxy residues being aryloxy having at least one free position ortho to the oxygen atom. Especially suitable are magnesium bis-phenoxides wherein the phenoxide residues may be unsubstituted or may be substituted in any or all of the positions, other than both the 2- and 6-positions, by substituents which do not interfere with the course of the reaction and which preferably are electron-donating or weakly electron-withdrawing.

The invention is especially concerned with the use of magnesium bis-phenoxides derived from phenols of the formula:

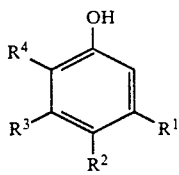

(1)

wherein each of $R^1$, $R^2$, $R^3$ and $R^4$, independently, represents a hydrogen or halogen atom or an alkyl, cycloalkyl, aralkyl, aryl, alkaryl, akoxy, aryloxy or acyl group, for the preparation of 2-hydroxyarylaldehydes of the formula:

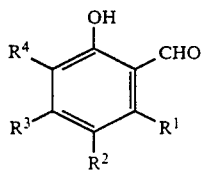

(2)

Each of the various hydrocarbyl, hydrocaryloxy and acyl groups which may be represented by $R^1$, $R^2$, $R^3$ and $R^4$ suitably contains up to 36 carbon atoms, for example from 5 to 22 carbon atoms.

Particular mention may be made of magnesium bis-phenoxides derived from phenols of the formula:

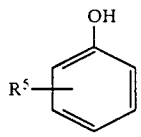

(3)

wherein $R^5$ represents hydrogen or a $C_{1-22}$ alkyl radical, said compounds being used in the preparation of 2-hydroxyarylaldehydes of the formula:

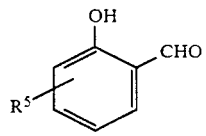

(4)

Preferably, $R^5$ is a $C_{7-12}$ alkyl radical.

The magnesium bis-phenoxides derived from phenols of Formula 1 or Formula 3 may be regarded as compositions containing structures of Formula 5 or Formula 6 respectively as well as related but more complex structures containing more than one magnesium atom per molecule. In structures of Formula 5:

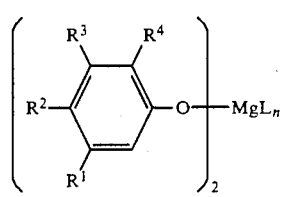

(5)

each of $R^1$, $R^2$, $R^3$ and $R^4$ is as defined above, L represents a ligand molecule derived from another component of the reaction mixture and n represents an integer from 1 to 6.

In structures of Formula 6:

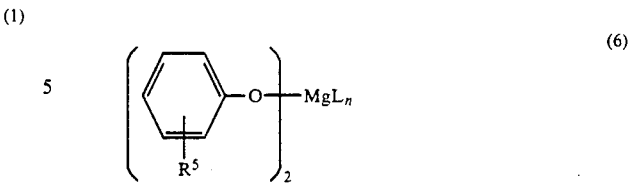

(6)

$R^5$, L and n are as defined above.

Components of the reaction mixture which may provide the ligand molecules L include the co-solvent, formaldehyde and the methanol by-product and mixtures thereof.

It is particularly convenient, however, to use a magnesium bis-aryloxide which, because of its method of preparation, already contains appropriate ligand molecules.

Thus, it is preferred to use a magnesium bis-hydrocarbyloxide which has been prepared by the method described by Ramirez et al in Synthesis, 1979, 71, that is to say by reacting a magnesium alkoxide of the formula:

$$Mg(OR^6)_2 \qquad (7)$$

wherein $R^6$ represents an alkyl, for example a $C_{1-4}$-alkyl, radical, especially methyl, with up to two moles of a phenol having at least one unsubstituted position adjacent to the phenolic hydroxyl group, for example a phenol of Formula 1 or Formula 3. Preferred ratios are from 0.9 to 2, especially from 1.5 to 2, typically about 1.66, moles of phenol per mole of magnesium alkoxide.

The magnesium bis-aryloxides, when used in the method of the invention, contain two aryloxy residues per magnesium atom and are believed also to contain one or more ligand molecules or groups, for example methanol molecules, such that they correspond or are structurally analogous to Formula 5. It is to be understood, however, that the present invention is not based upon any theory as to the precise structure of the magnesium bis-aryloxides and is to be regarded as relating to the use of said bis-aryloxides whether in the form of complexes of Formula 5 or not.

Other magnesium bis-hydrocarbyloxides which may be used in the method of the invention include compounds containing one aryloxy and one other hydrocarbyloxy, for example alkoxy, residue per magnesium atom. Such bis-hydrocarbyloxides may be obtained, for example, by reacting one mole of a magnesium alkoxide of Formula 7 with approximately one mole of a phenol having at least one unsubstituted position adjacent to the phenolic hydroxyl group and may, if desired, be used alone or in admixture with the aforementioned bis-aryloxides.

The formaldehyde used in the method of the invention may be in the form of free gaseous formaldehyde or a solution in an anhydrous solvent or a formaldehyde-liberating compound, that is to say a compound capable of liberating formaldehyde under the conditions employed in the method of the invention. Suitable formaldehyde-liberating compounds include polymeric forms of formaldehyde such as paraformaldehyde. It is preferred to add the formaldehyde or formaldehyde-liberating compound gradually (continuously or discontinuously) to the bis-aryloxide in the solvent system.

The formaldehyde or formaldehyde-liberating compound is generally employed in the method of the invention in an amount of at least two moles, expressed as formaldehyde (HCHO), per mole of phenol present in the bis-hydrocarbyloxide. Preferred ratios are from 2 to 3, typically about 2.75 moles of formaldehyde per mole of phenol in the bis-hydrocarbyloxide. The co-solvent is suitably used in an amount not exceeding 5 moles per mole of bis-hydrocarbyloxide, preferred amounts being in the range from 1 to 2 moles per mole of bis-hydrocarbyloxide. These amounts include any co-solvent already present as ligand in the bis-hydrocarbyloxide. Since methanol is a by-product of the reaction, conversion and yield may be maximised by removing this methanol and any other volatile by-products by distillation during the course of the reaction so as to maintain the co-solvent/bis-aryloxide ratio at the optimum level.

At the end of the reaction, the 2-hydroxyarylaldehyde product may be isolated from the reaction mixture using conventional methods. Thus, the cooled reaction mixture may be drowned into cold dilute acid and the aqueous mixture may then be extracted with a suitable organic solvent such as toluene which may then be removed by distillation leaving the crude 2-hydroxyarylaldehyde which may be subjected to further conventional purification as desired.

The method of the invention is particularly suitable for use in the preparation of 5-alkylsalicylaldehydes of the formula:

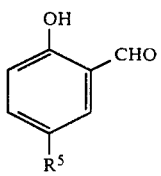

(8)

wherein $R^5$ is as defined above, from the corresponding magnesium bis-(4-alkylphenoxides). Thus, 4-nonylphenol (a mixture of isomers derived from phenol and propylene trimer) may be converted to the corresponding magnesium bis-phenoxide which may be used in the method of the invention to prepare 5-nonylsalicylaldehyde, an intermediate in the manufacture of the metal extractant 5-nonylsalicylaldoxime.

The invention is illustrated but not limited by the following Examples.

EXAMPLE 1

To a solution of magnesium methoxide (11.8 g 0.137 mole) in methanol (250 ml) being stirred at reflux temperature (65° C.) was added a solution of nonylphenol (55 g 0.25 mole) in methanol (100 ml) and stirring at reflux temperature was continued for a further 1.5 h.

Most of the methanol was then removed by distillation and toluene (500 ml) was added. Distillation of methanol and toluene was carried out until the internal temperature reached 105° C. The mixture was cooled to 90° C. and dimethylformamide (18.5 g 0.25 mole) was added. Paraformaldehyde (30.0 g 1.0 mole) was added slowly over 0.5 h at 90° C. with removal of distillate and then the reaction mixture was stirred at 95°-100° C. for a further 3 h.

The mixture was cooled, drowned into a mixture of cold water (1 l) and $H_2SO_4$ (40 g) and stirred for 0.5 h then extracted with toluene. The toluene was removed by distillation under vacuum leaving crude 5-nonylsalicylaldehyde.

Weight of crude product (62-66 g) Results

Strength by GC (75-80%) Average of 6 preparations Yield (75-85%)

The nonylphenol used in this Example was a mixture comprising approximately 5% p-octylphenol, 94% p-nonylphenol and 1% p-decylphenol.

EXAMPLE 2

Methanol (225 g) and toluene (86 g) were charged to a 2 liter glass reaction vessel followed by magnesium raspings (2.92 g). An activator solution (10 g) was added to activate the magnesium and the mixture was heated to reflux temperature (65° C.) to achieve magnesium dissolution with evolution of hydrogen gas. The mixture was maintained at reflux temperature for 0.5 h and then further magnesium was added in four portions (4×2.92 g) over a total period of 1.5 h, each portion being added once hydrogen evolution from the previous portion had subsided. The mixture was then heated under reflux for a further hour to ensure complete magnesium dissolution, 4-nonylphenol (224 g) was added and the mixture heated under reflux for 1 h to achieve nonylphenol magnesium salt formation. The activator solution was taken from a composition (1116 g) containing nonylphenol magnesium salt (461 g), magnesium methoxide (17.3 g), toluene (194 g) and methanol (443.7 g).

Toluene (800 g) was added and methanol-toluene azeotrope (286 g) was removed by distillation until the reaction mixture temperature reached 100° C. An agitated slurry of paraformaldehyde (92.8 g) in toluene (150 g) was added to the resulting toluene solution of the nonylphenol magnesium salt at 95° C. over 3 h with removal of toluene and volatile by-product distillates (111 g). On completion of paraformaldehyde addition, the reaction mixture was heated to 95°-100° C. for 1 h to ensure completion of reaction and the mixture was then cooled to 30°-40° C.

The reaction mixture was drowned out into a mixture of cold water (1000 g) and sulphuric acid (122.5 g), maintaining the temperature of the mixture below 40° C. The whole mixture was stirred at ambient temperature for 2 h to ensure complete hydrolysis of reaction intermediates, the mixture was allowed to settle and the upper (organic) layer was separated from the lower (aqueous) layer.

The organic layer was washed with water until acid-free and toluene was then removed by distillation under reduced pressure to leave the crude 5-nonylsalicylaldehyde as a yellow oil (253 g). The aldehyde was purified by distillation at 170°-225° C./20 mm Hg.

EXAMPLE 3

Magnesium ethoxide powder (17 g) was added to a mixture of 4-nonylphenol (55 g) and toluene (400 ml) at room temperature. The mixture was then heated to 90°-95° C. and was then stirred at that temperature for 2 ½ h. The temperature was then raised to 100° C. and distillate (5 ml) was taken off.

After cooling to 90° C., paraformaldehyde (26.3 g) was added in four portions and stirring was continued for 2 h at 95° C.

The hot mixture was drowned into a mixture of cold water (1.5 l) and concentrated sulphuric acid (40 g) and the whole was stirred overnight at room temperature. The mixture was then extracted with toluene and the toluene extract was washed with water until acid-free. The toluene was then removed by distillation under reduced pressure leaving crude 5-nonylsalicylaldehyde (62.7 g).

EXAMPLE 4

Phenol (48g 0.5 Mole) and 323.75 g of an 8% solution of magnesium methoxide (0.3 mole) in methanol were heated from 20° C. to 65° C. over 15 minutes and then stirred at reflux temperature for a further hour.

Half of the methanol was then removed by distillation and toluene (500 g) was added. The mixture was heated until the internal temperature reached 100° C. (approx 1 hour) and most of the methanol had been removed as its azeotrope with toluene.

Paraformaldehyde (46.4 g 1.5 mole) was slowly added in portions over 2 hours, maintaining the internal temperature at 102°-105° C. and removing low boiling distillates. The reaction mixture was stirred at 105° C. for a further hour, cooled to 25° C. and then slowly added to 588 g of 10% sulphuric acid, keeping the temperature below 35° C. After stirring for 5 hours, the organic layer was separated from the aqueous layer and vacuum topped to give salicylaldehyde in 78% yield.

EXAMPLE 5

The procedure described in Example 4 was followed, replacing the phenol (48 g) by 4-octylphenol (105 g 0.5 mole). During addition of the paraformaldehyde, the internal temperature was maintained at 95°-98° C. and the reaction mixture was stirred at 98° C. for a further hour. In other respects, the conditions were as described in Example 4. The product, 5-octylsalicylaldehyde, was obtained in 85% yield.

EXAMPLE 6

In a 500 ml round bottom three necked flask equipped with a mechanical stirrer, thermometer, and reflux condenser were charged 3.65 g (0.15 mole) Mg turnings, 25 ml toluene and 75 ml dry methanol. To this was added 2.5 ml Of Mg(OMe)$_2$ (8% in methanol) and the reaction heated to reflux under N$_2$. After several minutes, hydrogen evolution was noted. The reaction was refluxed for 1 hr. 4-heptylphenol (48.0 g, 0.25 mole) was then added and the mixture refluxed under N$_2$ for 2 hours. Toluene (200 ml) was then added and a fractionating column was connected to the reaction flask. Methanol was removed as an azeotrope with toluene until a pot temperature of 100° C. was achieved. At this time the solution had become quite viscous. The temperature was reduced to 92° C. and the fractionating column removed. A slurry of paraformaldehyde (23.2 g, 0.77 mole) in 75 ml toluene was added in portions over 1 hr. The reaction was held at 95° C. for an additional 1 hr. The volatiles (27 ml) were removed by simple distillation (BP 48°-53° C.). The reaction contents were poured into 400 ml 7.7% sulphuric acid and stirred at ambient temperature for 1 hour. The contents were transferred to a separatory funnel and the aqueous phase removed. The aqueous phase was extracted with 100 ml toluene. The organic phases were combined and washed 4 times with 100 ml water. The solvent was removed by rotary evaporation to yield 53.9 g light yellow oil. HPLC analysis indicated 87% 5-heptylsalicylaldeyde, and 9% of a bridged methylene species. Only traces of heptylphenol were detected. Overall yield: 85% based on heptylphenol charged.

EXAMPLE 7

The procedure described in Example 6 was repeated, replacing the heptylphenol (48.0 g) by 4-dodecylphenol (72 g 0.29 mole). The product was a light yellow oil (79.7 g). HPLC analysis indicated 78% 5-dodecylsalicylaldehyde and 20% of a methylene bridged species. Overall yield: 78%.

EXAMPLE 8

The procedure described in Example 6 was repeated, replacing the heptylphenol (48.0 g) by 2,4 dimethylphenol (30.5 g 0.25 mole). The product was a light yellow oil (34.6 g). HPLC analysis indicated the product consisted of 72% 3,5-dimethylsalicylaldehyde and 20 % of a methylene bridged species. Yield of 3,5-dimethylsalicylaldehyde: 66%.

EXAMPLE 9

The procedure described in Example 6 was repeated, replacing the heptylphenol (48.0 g) by 4-methoxyphenol (31.0 g 0.25 mole). The product was a light yellow oil (36.0 g). HPLC showed a major peak consistent with 5-methoxysalicylaldehyde. Yield: 94%.

EXAMPLE 10

The procedure described in Example 6 was repeated, replacing the heptylphenol (48.0 g) by 4-chlorophenol (32.2 g 0.25 mole). The product was a dark oil (32.3 g) which solidified on standing. NMR and HPLC analysis indicated the product contained 40% 5-chlorosalicylaldehyde. Yield: 33%.

EXAMPLE 11

A solution of 4-methylphenol (1000 g, 9.26 mole) in toluene (2.5l) was added to magnesium methoxide (522 g, 6.05 mole) in methanol (8.0l) and refluxed for 1 hour. Further toluene (8.5l) was added and the mixture distilled slowly until the internal temperature reached 95° C.

A slurry of paraformaldehyde (865 g, 28.8 moles) in toluene was added at 95° C. over a period of 3 hours followed by heating at 95°-1000° C. for a further 3 hours. The reaction mixture was cooled to 30° C., diluted with toluene (10l) and any insoluble material removed by filtration. The toluene solution was washed with 2M aqueous sulphuric acid (10l) and then water (5l) three times.

The solvent was removed by distillation in vacuo. n-Hexane (95l) was added and then removed by distillation to leave the product 5-methylsalicylaldehyde (2-hydroxy-5-methylbenzaldehyde identified by nmr) as a pale yellow semi-solid oil.

EXAMPLE 12

Methanol (449 g) toluene (194 g) and 10 ml of a 41% solution of the magnesium salt of nonylphenol in 70/30 methanol/toluene were charged to a 3 liter parallel-sided jacketed vessel. The mixture was heated to reflux temperature (64° C.) and magnesium turnings were added in four portions (4×7.3 g) over 1 hour. After a further 1 hour at reflux temperature, all of the magnesium had dissolved and 4-nonylphenol (448 g) was added and the mixture heated under reflux (66° C.) for another hour.

Toluene (416 g) was added and methanol/toluene azeotrope (574 g) was removed by distillation until the internal temperature reached 90°-95° C. A slurry of paraformaldehyde (165 g) in toluene (251 g) was then added slowly over 3 hours to the mixture at 95°–100° C. with concurrent distillation of low boiling reaction products. The mixture was then stirred at 95°–100° C. until the reaction was complete.

The reaction mixture was drowned out into a mixture of water (1000 g) and 98% sulphuric acid (250 g) and stirred vigorously at room temperature for 2 hours. The mixture was then allowed to settle and the upper (organic) layer was separated from the lower (aqueous) layer.

The organic layer was washed with water (2×1000ml) until acid free and toluene was then removed by rotary evaporation at 20 mm Hg up to 90° C. leaving 5-nonylsalicylaldehyde as a pale yellow oil (500 g of 85% strength, yield=86%).

EXAMPLE 13

Methanol (112 g) and 10ml of an 8% solution of magnesium methoxide in methanol were charged to a one liter round-bottomed flask and heated to reflux temperature (64° C.) after which magnesium (7.3 g) was added. After 1 hour, all of the magnesium had dissolved and 4-nonylphenol (112 g) was added and the mixture stirred under reflux (66° C.) for another hour.

Xylene (130 g) was added and methanol/xylene azeotrope (86 g) was removed by distillation until an internal temperature of 104° C. had been reached.

A slurry of paraformaldehyde (45 g) in xylene (65 g) was then added slowly over 1 hour to the mixture at 105° C. with concurrent distillation of volatile by-products. The mixture was then stirred at 105°–110° C. until the reaction was complete.

The reaction mixture was drowned out into a mixture of water (250 g) and 98% sulphuric acid (63 g) and stirred vigorously at room temperature for 2 hours. The mixture was then allowed to settle and the upper (organic) layer was separated from the lower (aqueous) layer.

The organic layer was washed with water (2×250ml) until acid-free and xylene was then removed by rotary evaporation at 20 mm Hg up to 90° C. leaving 5-nonylsalicylaldehyde as a pale yellow oil (120 g of 80% strength, yield=78%).

EXAMPLE 14

A solution of magnesium methoxide (292 g of 8% solution in methanol, 0.275 mol) was added over 10 minutes to a stirred solution of p-nonylphenol (55 g, 0.25 mol) in methanol (50 ml). The stirred mixture was heated to reflux temperature, the bulk of the methanol was removed by distillation, toluene (500 ml) was added and toluene:methanol azeotrope was removed by fractional distillation until the temperature of the reaction mixture rose to 100° C. The mixture was cooled to 90° C. and an agitated slurry of paraformaldehyde fine powder (26.25 g, 0.875 mol) in toluene (100 ml) was added evenly over 1 hour to the reaction mixture at 90°–100° C. with removal of volatile by-products by distillation. Stirring was continued at 100° C. for a further hour, the mixture was cooled to 45° C. and was added to a premixed solution of concentrated sulphuric acid (62.5 g, 0.875 mol) in water (1 liter). The resulting mixture was stirred at ambient temperature for 1 hour, the phases were separated and the aqueous phase was extracted with toluene (200 ml). The toluene extract was combined with the original organic phase and toluene was removed by distillation under reduced pressure to give the crude 2-hydroxy-5-nonyl benzaldehyde as a yellow oil (58.5 g).

I claim:

1. A method for the preparation of a 2-hydroxyarylaldehyde which comprises reacting a magnesium bis-hydrocarbyloxide derived at least in part from a hydroxyaromatic compound having at least one free position ortho to the hydroxyl group with formaldehyde or a formaldehyde-liberating compound under substantially anhydrous conditions.

2. A method according to claim 1 which comprises reacting the magnesium bis-hydrocarbyloxide with the formaldehyde or formaldehyde-liberating compound in the presence of a substantially anhydrous solvent mixture comprising an aromatic hydrocarbon or a chlorinated aromatic hydrocarbon and as co-solvent, a polar solvent selected from the group consisting of polar aprotic solvents, tertiary bases, ethers and lower alkanols.

3. A method according to claim 2 wherein the inert organic solvent comprises an aromatic hydrocarbon or a chlorinated aromatic hydrocarbon.

4. A method according to claim 3 wherein the aromatic hydrocarbon comprises toluene or xylene.

5. A method according to any one of claims 2 to 4 wherein the co-solvent comprises a polar aprotic solvent or a lower alkanol.

6. A method according to claim 5 wherein the lower alkanol comprises methanol.

7. A method according to any one of claims 1 to 6 wherein the magnesium bis-hydrocarbyloxide is a magnesium bis-phenoxide wherein the phenoxide residues may be unsubstituted or may be substituted in any or all of the positions, other than both the 2- and 6- positions, by substituents which do not interfere with the course of the reaction.

8. A method according to claim 7 wherein the magnesium bis-phenoxide is derived from a phenol of the formula:

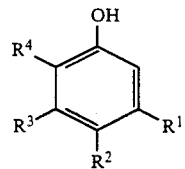

(1)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy or acyl group.

9. A method according to claim 8 wherein each of the alkyl, cycloalkyl, aralkyl, aryl, alkaryl, alkoxy, aryloxy or acyl groups which may be represented by $R^1$, $R^2$, $R^3$ and $R^4$ contains from 5 to 22 carbon atoms.

10. A method according to claim 8 wherein the magnesium bis-phenoxide is derived from a phenol of the formula:

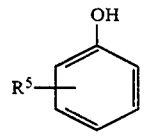

(3)

wherein $R^5$ represents hydrogen or a $C_{1-22}$-alkyl radical.

11. A method according to claim 10 wherein $R^5$ is a $C_{7-12}$-alkyl radical.

12. A method according to any one of claims 1 to 11 wherein the magnesium bis-hydrocarbyloxide is the product of reacting a magnesium alkoxide of the formula:

$$MG(OR^6)_2 \qquad (5)$$

wherein $R^6$ represents an alkyl radical with up to two moles of a phenol having at least one unsubstituted position ortho to the hydroxyl group.

13. A method according to claim 12 wherein the magnesium bis-hydrocarbyloxide is the product of reacting the magnesium alkoxide with from 0.9 to 2 moles of phenol per mole of magnesium alkoxide.

14. A method according to claim 13 wherein the magnesium bis-hydrocarbyloxide is the product of reacting the magnesium alkoxide with from 1.5 to 2 moles of phenol per mole of magnesium alkoxide.

15. A method according to any one of claims 12 to 14 wherein $R^6$ is a $C_{1-4}$- alkyl radical.

16. A method according to claim 15 wherein the magnesium alkoxide is magnesium methoxide.

17. A method according to any one of claims 1 to 16 wherein the formaldehyde-liberating compound is paraformaldehyde.

18. A method according to any one of claims 1 to 17 wherein the amount of formaldehyde or formaldehyde-liberating compound used is at least 2 moles HCHO per mole of phenol present in the magnesium bis-hydrocarbyloxide.

19. A method according to claim 18 wherein the molar ratio of formaldehyde to phenol in the bis-hydrocarbyloxide is from 2 to 3.

20. A method according to any one of claims 2 to 19 wherein the co-solvent is used in an amount not exceeding 5 moles per mole of magnesium bis-hydrocarbyloxide.

21. A method according to claim 20 wherein the co-solvent is used in an amount of from 1 to 2 moles per mole of bis-hydrocarbyloxide.

22. A method according to any one of claims 1 to 21 wherein the magnesium bis-hydrocarbyloxide is magnesium bis-(4-nonylphenoxide).

* * * * *